United States Patent
O'Malley et al.

(10) Patent No.: US 11,633,429 B2
(45) Date of Patent: *Apr. 25, 2023

(54) TARGETING OF SRC-3 IN IMMUNE CELLS AS AN IMMUNOMODULATORY THERAPEUTIC FOR THE TREATMENT OF CANCER

(71) Applicant: Baylor College of Medicine, Houston, TX (US)

(72) Inventors: Bert W. O'Malley, Houston, TX (US); Sang Jun Han, Houston, TX (US); David M. Lonard, Houston, TX (US); Bryan Nikolai, Houston, TX (US); Prashi Jain, Houston, TX (US); Yosef Gilad, Houston, TX (US); Clifford Dacso, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/650,645

(22) Filed: Feb. 10, 2022

(65) Prior Publication Data

US 2022/0160773 A1 May 26, 2022

Related U.S. Application Data

(62) Division of application No. 17/446,282, filed on Aug. 27, 2021.

(60) Provisional application No. 63/106,770, filed on Oct. 28, 2020.

(51) Int. Cl.
| | |
|---|---|
| *C12N 5/0783* | (2010.01) |
| *C12N 15/113* | (2010.01) |
| *C12N 15/90* | (2006.01) |
| *A61K 35/17* | (2015.01) |
| *A61K 45/06* | (2006.01) |
| *A61P 35/00* | (2006.01) |

(52) U.S. Cl.
CPC .............. *A61K 35/17* (2013.01); *A61K 45/06* (2013.01); *A61P 35/00* (2018.01); *C12N 5/0637* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 6,156,571 A | 12/2000 | Bennett et al. | |
| 9,683,237 B2 | 6/2017 | Rao et al. | |
| 9,782,418 B2 | 10/2017 | Lee et al. | |
| 10,875,841 B2 | 12/2020 | O'Malley et al. | |
| 11,136,562 B2 | 10/2021 | Taunton et al. | |
| 11,253,517 B2 | 2/2022 | O'Malley et al. | |
| 2003/0104975 A1 | 6/2003 | Auwerx et al. | |
| 2004/0259114 A1 | 12/2004 | Riegel et al. | |
| 2004/0265295 A1 | 12/2004 | Anderson et al. | |
| 2013/0064881 A1 | 3/2013 | Nemunaitis et al. | |
| 2013/0259925 A1 | 10/2013 | Rao et al. | |
| 2013/0266639 A1 | 10/2013 | Rao et al. | |
| 2015/0307885 A1 | 10/2015 | Rao et al. | |
| 2018/0002371 A1 | 1/2018 | Wang et al. | |
| 2018/0072814 A1 | 3/2018 | Lu et al. | |
| 2018/0203017 A1 | 7/2018 | Ting et al. | |
| 2018/0265444 A1 | 9/2018 | Lonard et al. | |
| 2020/0085967 A1 | 3/2020 | Donald | |

FOREIGN PATENT DOCUMENTS

| | | |
|---|---|---|
| CN | 106661576 A | 5/2017 |
| EP | 3811950 A1 | 4/2021 |
| WO | 1999/032621 A2 | 7/1999 |
| WO | 2013/148824 A1 | 10/2013 |
| WO | 2018/223867 A1 | 12/2018 |
| WO | 2021/055517 A1 | 3/2021 |

OTHER PUBLICATIONS

Ayala G, Yan J, Li R, Ding Y, Thompson TC, Mims MP, Hayes TG, MacDonnell V, Lynch RG, Frolov A, Miles BJ, Wheeler TM, Harper JW, Tsai MJ, Ittmann MM, Kadmon D. Bortezomib-mediated inhibition of steroid receptor coactivator-3 degradation leads to activated Akt. Clin Cancer Res. 2008;14(22);7511-8. Epub Nov. 18, 2008.

Coarfa C, Fiskus W, Eedunuri VK, Rajapakshe K, Foley C, Chew SA, Shah SS, Geng C, Shou J, Mohamed JS, O'Malley BW, Mitsiades N. Comprehensive proteomic profiling identifies the androgen receptor axis and other signaling pathways as targets of microRNAs suppressed in metastatic prostate cancer. Oncogene. 2016;35(18):2345-56.

Coste A, Antal MC, Chan S, Kastner P, Mark M, O'Malley BW, Auwerx J. Absence of the steroid receptor coactivator-3 induces B-cell lymphoma EMBO J. 2006;25(11):2453-64. Epub May 6, 2006.

Eedunuri VK, Rajapakshe K, Fiskus W, Geng C, Chew SA, Foley C, Shah SS, Shou J, Mohamed JS, Coarfa C, O'Malley BW, Mitsiades N. miR-137 Targets p160 Steroid Receptor Coactivators SRC1, SRC2, and SRC3 and Inhibits Cell Proliferation. Mol Endocrinol. 2015;29(8):1170-83. doi: 10.1210/me.2015-1080.

(Continued)

*Primary Examiner* — G. R. Ewoldt
*Assistant Examiner* — Marianne DiBrino
(74) *Attorney, Agent, or Firm* — Norton Rose Fulbright US LLP

(57) ABSTRACT

The present disclosure concerns methods and compositions related to cancer treatment comprising targeting of SRC-3 in immune cells, including T cells such as T regulatory cells. The targeting of SRC-3 in T regulatory cells in particular is effective to eradicate tumors in mammals. In specific cases, the T regulatory cells are subjected to CRISPR ex vivo to produce cells suitable for adoptive cell transfer. In some cases, one or more agents that target SRC-3 are also administered to the individual and/or are exposed to the cells prior to administration.

7 Claims, 8 Drawing Sheets

Specification includes a Sequence Listing.

(56) References Cited

OTHER PUBLICATIONS

Geng C, He B, Xu L, Barbieri CE, Eedunuri VK, Chew SA, Zimmermann M, Bond R, Shou J, Li C, Blattner M, Lonard DM, Demichelis F, Coarfa C, Rubin MA, Zhou P, O'Malley BW, Mitsiades N. Prostate cancer-associated mutations in speckle-type POZ protein (SPOP) regulate steroid receptor coactivator 3 protein turnover. Proc Natl Acad Sci U S A. 2013;110(17):6997-7002.

Tanaka et al. "Regulation of Pathogenic T Helper 17 Cell Differentiation by Steroid Receptor Coactivator-3", Cell Reports, May 22, 2018, vol. 23, No. 8, p. 2318-2329.

Tien JC, Liu Z, Liao L, Wang F, Xu Y, Wu YL, Zhou N, Ittmann M, Xu J. The steroid receptor coactivator-3 is required for the development of castration-resistant prostate cancer. Cancer Res 2013;73(13):3997-4008. Epub May 8, 2013.

Vandenbon A, Dinh VH, Mikami N, Kitagawa Y, Teraguchi S, Ohkura N, Sakaguchi S. Immuno-Navigator, a batch-corrected coexpression database, reveals cell type-specific gene networks in the immune system. Proc Natl Acad Sci U S A. 2016;113(17):E2393-402.

Wang Y, Lonard DM, Yu Y, Chow DC, Palzkill TG, O'Malley BW. Small molecule inhibition of the steroid receptor coactivators, SRC-3 and SRC-1. Mol Endocrinol. 2011;25(12):2041-53. Epub Nov. 5, 2011.

Wu C, Orozco C, Boyer J, Leglise M, Goodale J, Batalov S, Hodge CL, Haase J, Janes J, Huss JW, 3rd, Su AI. BioGPS: an extensible and customizable portal for querying and organizing gene annotation resources. Genome Biol. 2009;10(11);R130, 8 pages.

Yan J, Erdem H, Li R, Cai Y, Ayala G, Ittmann M, Yu-Lee LY, Tsai SY, Tsai MJ. Steroid receptor coactivator-3/AIB1 promotes cell migration and invasiveness through focal adhesion turnover and matrix metalloproteinase expression. Cancer Res. 2008;68(13):5460-8. Epub Jul. 3, 2008.

Yan J, Yu CT, Ozen M, Ittmann M, Tsai SY, Tsai MJ. Steroid receptor coactivator-3 and activator protein-1 coordinately regulate the transcription of components of the insulin-like growth factor/AKT signaling pathway. Cancer Res. 2006,66(22):11039-46. Epub Nov. 17, 2006.

Zhou HJ, Yan J, Luo W, Ayala G, Lin SH, Erdem H, Ittmann M, Tsai SY, Tsai MJ. SRC-3 is required for prostate cancer cell proliferation and survival Cancer Res. 2005;65(17):7976-83. Epub Sep. 6, 2005.

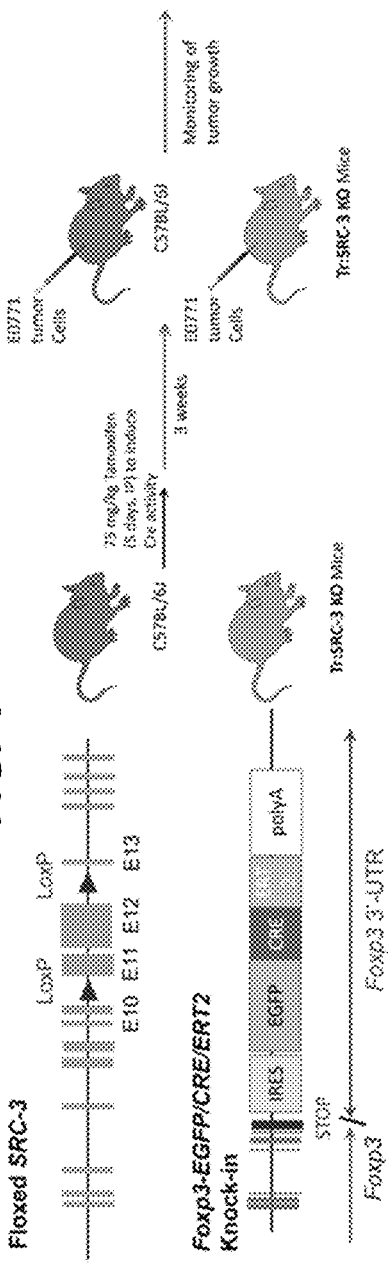
FIG. 4A
FIG. 4B
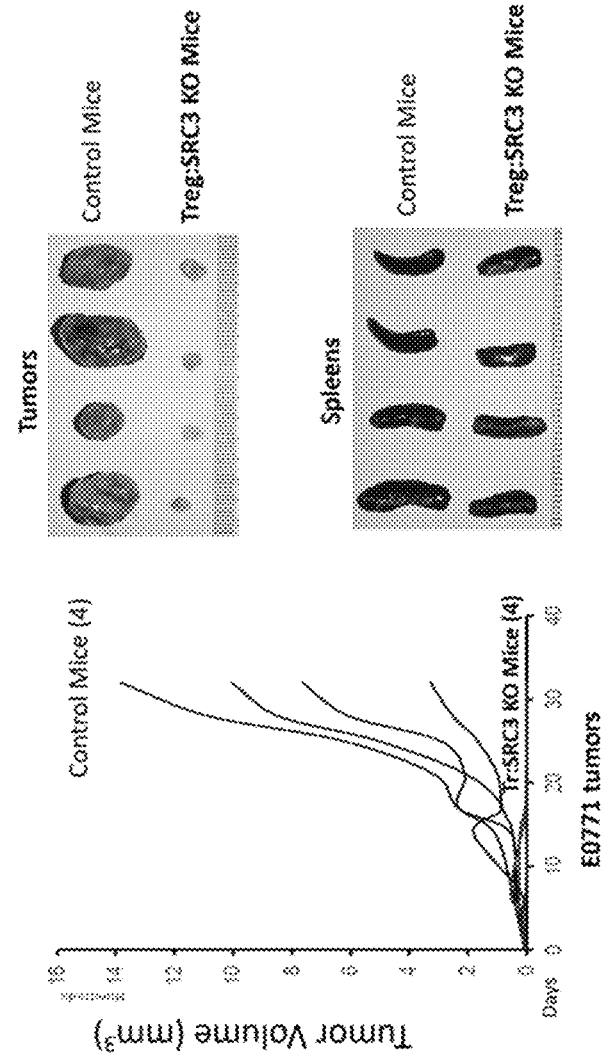
FIG. 4C

TARGETING OF SRC-3 IN IMMUNE CELLS AS AN IMMUNOMODULATORY THERAPEUTIC FOR THE TREATMENT OF CANCER

This application is a divisional of U.S. Non-Provisional application Ser. No. 17/446,282 filed Aug. 27, 2021, which claims priority to U.S. Provisional Application Ser. No. 63/106,770 filed Oct. 28, 2020, both of which are incorporated by reference herein in their entirety.

STATEMENT REGARDING FEDERALLY SPONSORED RESEARCH OR DEVELOPMENT

This invention was made with government support under W81XWH-13-1-0285 awarded by the Department of Defense and under HD008188 awarded by the National Institutes of Health. The government has certain rights in the invention.

INCORPORATION OF SEQUENCE LISTING

The instant application contains a Sequence Listing which has been submitted electronically in ASCII format and is hereby incorporated by reference in its entirety. Said ASCII copy, created on Feb. 10, 2022, is named BAYM_P0326USD2_1001199029_SL.txt and is 1,292 bytes in size.

TECHNICAL FIELD

Embodiments of the disclosure concern at least the fields of cell biology, molecular biology, immunology, and medicine, including cancer medicine.

BACKGROUND

Steroid receptor coactivator-3 (SRC-3) functions as a key driver of breast cancer (BC) proliferation, metastasis and resistance to standard and endocrine-based cancer therapy. As an oncogene, SRC-3 acts as a pleiotropic coactivator for nuclear receptors and multiple other transcription factors that drive programs required for cancer cell proliferation and metastasis. Importantly, SRC-3 also plays an important role in regulation of the host immune system.

The present disclosure addresses a long-felt need in the art of providing effective cancer therapies by targeting SRC-3 in a unique manner.

BRIEF SUMMARY

The present disclosure is directed to systems, methods, and compositions for treating, delaying progression of, delaying onset of, or reducing the risk of getting cancer of any kind. In particular embodiments, the disclosure concerns adoptive cell transfer in which the cells being administered to an individual in need thereof are immune cells that (1) have disruption of expression of endogenous SRC-3; and/or (2) have had exposure to one or more agents that target SRC-3. In specific embodiments, the immune cells are CD4+ cells, including T regulatory cells (Treg) that are CD4+.

Current Treg-targeting immune checkpoint inhibitors are mostly focused on surface proteins (receptors) that disrupt their cell surface interactions with other immune cells. The present disclosure distinguishes from this, because SRC-3 as a Treg gene target is a nuclear protein that functions to regulate Treg nuclear gene expression programs. As a consequence of its role as a transcriptional master regulator, it is shown herein that ablation of SRC-3 in a mouse genetic model can modulate Treg function in a way that promotes tumor eradication while avoiding the otherwise severe side effects that are frequently observed with established immune checkpoint inhibitors. In specific embodiments, the present disclosure concerns a CRISPR-based approach to target the SRC-3 gene in immune cells, including for genetically modified Treg cells, to be used for adoptive transfer into individuals with cancer. Thus, the present disclosure provides a unique way to support immune-system based tumor eradication.

In one embodiment, there is an engineered immune cell, comprising disruption of steroid receptor coactivator-3 (SRC-3). In specific embodiments, the immune cell is a T cell, such as a T regulatory cell. The T cell may be CD4+, CD25+, and/or FOXP3+. In certain embodiments, the disruption is further defined as the immune cell being genetically modified to have reduced level of expression of SRC-3 or having essentially no expression of SRC-3. In specific cases, the immune cell is engineered using one or more guide RNAs and a Cas9 enzyme. The immune cell may be autologous, allogeneic, or syngeneic with respect to an individual.

In certain embodiments, there is a composition, comprising: (a) any immune cell encompassed herein; and (b) one or more agents that target SRC-3. In some cases, (a) and (b) are in different formulations, although they may be in the same formulation. In specific embodiments, the agent that targets SRC-3 is a small molecule inhibitor, an antibody, a protein, a nucleic acid, or a combination thereof. The small molecule inhibitor of SRC-3 may be Bufalin, gossypol, Verrucarin A, SI-2, SI-10, SI-12, a functional derivative thereof, or a combination thereof. The antibody may be a monoclonal antibody or polyclonal antibody, and specific examples include 5E11, LS-C801929, PA1-845, AX15.3, PAS-29854, EPR4374(3), or a combination thereof.

In one embodiment, there is a method of treating cancer in an individual, comprising the step of administering to the individual a therapeutically effective amount any cells encompassed herein. The cancer may be SRC-3+ cancer. The cancer may be breast, ovarian, endometrial, prostate, gastric, multiple myeloma, thyroid cancer, or pancreatic cancer.

In some cases, prior to the step of administering, the cells are exposed ex vivo to an effective amount of one or more agents that target SRC-3, such as a small molecule inhibitor (Bufalin, gossypol, Verrucarin A, SI-2, SI-10, SI-12, a functional derivative thereof, combination thereof), an antibody (monoclonal antibody or polyclonal or fragments, such as scFv), a protein, a nucleic acid, or a combination thereof. Specific antibodies include 5E11, LS-C801929, PA1-845, AX15.3, PAS-29854, EPR4374(3), or a combination thereof. In some cases, the individual is administered a therapeutically effective amount of an additional cancer therapy, such as surgery, radiation, chemotherapy, hormone therapy, drug therapy, protein therapy, immunotherapy, or a combination thereof. The additional cancer therapy may comprise one or more agents that target SRC-3. The cells and the additional cancer therapy may be administered to the individual at substantially the same time or at different times. The cells and the additional cancer therapy may or may not be in the same formulation. The cells may be administered intravenously, intraperitoneally, intraarterially, topically, by inhalation, intramuscularly, intrasternally, by intraarticular injection, or by infusion. The cells may be administered once or multiple times, and when they are administered multiple times, the duration between administrations is within 1-24 hours, 1-7 days, 1-4 weeks, or 1-12 months.

In one embodiment, there is a method of treating cancer in an individual, comprising the step of administering to the individual a therapeutically effective amount of any composition encompassed herein, including one that comprises (a) any immune cell encompassed herein; and (b) one or more agents that target SRC-3. In such cases, (a) and (b) may or may not be administered to the individual in different formulations and/or at the same or different times. When administered at different times, the duration between administrations of (a) and (b) may be within 1-24 hours, 1-7 days, 1-4 weeks, or 1-12 months. The composition may be administered to the individual once or multiple times and when the composition is administered to the individual at multiple times, the duration between administrations is within 1-24 hours, 1-7 days, 1-4 weeks, or 1-12 months. The cancer may be SRC-3+. The cancer may be of the breast, ovarian, endometrial, prostate, gastric, multiple myeloma, thyroid, or pancreatic cancer. In specific cases, prior to the step of administering, the cells in (a) are exposed ex vivo to an effective amount of one or more agents that target SRC-3.

In one embodiment, there is a method of producing any immune cells encompassed herein, comprising the step of disrupting expression of SRC-3 in the immune cells.

The immune cells may be T cells, including Tregs. In specific cases, the method is further defined as: (a) obtaining CD4+ T cells or CD4+ Tregs, respectively; and (b) exposing the CD4+ T cells or CD4+ Tregs, respectively, to one or more agents that disrupt expression of endogenous SRC-3 in the T cells or Tregs, respectively. In specific embodiments, the T cells or Tregs are obtained from the spleen, bone marrow, blood, plasma, or a combination thereof. The method may further comprise the step of obtaining T regulatory cells from the CD4+ T cells. In specific cases, the T regulatory cells are CD25+ and/or Fox3p+. In specific cases, the one or more agents that disrupt expression of endogenous SRC-3 in the T cells comprises nucleic acid. In particular aspects, the one or more agents that disrupt expression of endogenous SRC-3 in the T cells comprises CRISPR reagents. The method may further comprise the step of exposing the immune cells ex vivo to an effective amount of one or more agents that target SRC-3.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawings.

FIG. 2A. Representative plot of Ncoa3 (Src-3) probe intensities (two probes used) from selected tissues in the BioGPS genomics platform (10), showing that Src-3 is highly expressed in T cell lineages, with the highest expression in Foxp3+ CD4+ T cells (Tregs). FIG. 2B. Correlation of 296 NURSA-curated coregulators with Foxp3 expression in Tregs performed using Immuno-Navigator (12), a batch-corrected coexpression database. Ncoa3 is strongly correlated with Foxp3 expression in Tregs.

FIG. 3A. Silencing SRC-3 in human Tregs (from a healthy donor) reduces mRNA expression of Treg marker genes and immune checkpoint mediators. Donor Tregs were infected with lentiviral vectors expressing shRNA directed against luciferase (shLuc) or SRC-3 and mRNA levels were measured by RT-qPCR. FIG. 3B. SRC-3 can stimulate FOXP3 promoter function. SRC-3 coactivates FoxP3 promoter driven reporter activity in a transient transfection assay. 293T cells were transfected with FoxP3 promoter luciferase reporter (gift from GR Lee lab, Hwang et al 2016, Nat. Commun.) and increasing concentrations of a SRC-3 expression plasmid.

FIGS. 4A-4C: E0771 BC tumors are eradicated in a genetically engineered mouse model where SRC-3 is specifically deleted in Foxp3 expressing Treg cells. FIG. 4A. Floxed SRC-3 mice were backcrossed over 10 generations into the C57BL/6J background and crossed with a Foxp3-EGFP/CRE/ERT2 knock-in mouse also on a C57BL/6J background. Treatment with tamoxifen results in activation of Cre and excision of exons 11 and 12 of the SRC-3 gene. FIG. 4B. C57BL/6J control mice and Treg:SRC-KO mice were treated with tamoxifen for five days, then after an additional three weeks had 1×106 luciferase-expressing E0771 BC tumor cells injected into cleared mammary fat pads. FIG. 4C. Tumor volume was measured over a 32-day period (left). Images of tumors and spleens at the conclusion of studies are shown on the right.

FIG. 7A. Luciferase-labelled mammary gland carcinoma E0771 tumor cells were implanted into the cleared fat pads of wild type C57BL/6 mice. Following this, animals (2 per experimental group) were injected with SRC-3 KO Tregs, Control (Cont) Tregs, or no Tregs (No ACT, corresponding to wildtype cells) and tumor growth was monitored via luciferase tumor imaging. The elimination of tumors in the animals that received SRC-3KO Tregs is marked with arrows. Tumor luciferase imaging quantification is shown in FIG. 7B.

DETAILED DESCRIPTION

I. Examples of Definitions

Figure 1:
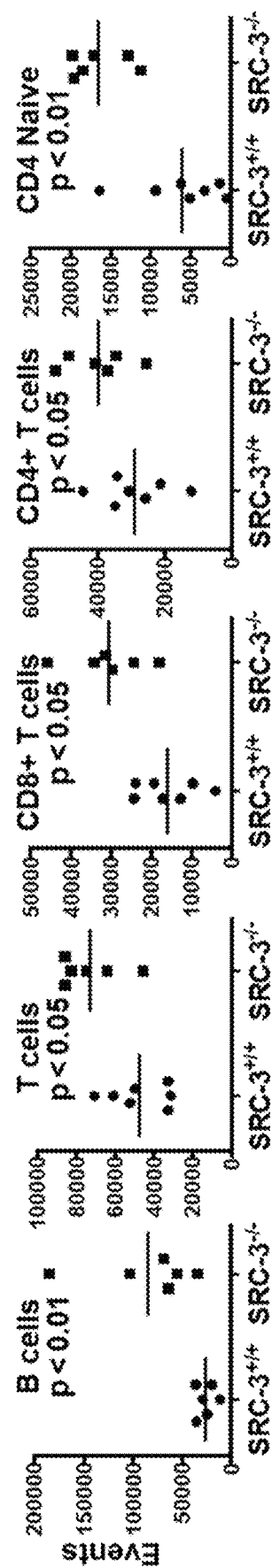
FIG. 1: Comprehensive immunophenotyping of Src-3 gene knockout (KO) mice reveals broad lymphocytosis Immunophenotyping of peripheral blood from aged (16-20 months) Src-3 KO mice (−/−, n=6) and wild-type littermates (+/+, n=7). There was a significant elevation of T and B cells, as well as specific subtypes, in SRC-3 knockout mice. There was no statistically significant difference in granulocytes, monocytes, eosinophils, macrophages, dendritic and NK cells (data not shown).

In keeping with long-standing patent law convention, the words "a" and "an" when used in the present specification in concert with the word comprising, including the claims, denote "one or more." As used in the specification and claims, the singular form "a", "an", and "the" include plural references unless the context clearly dictates otherwise. For example, the term "a nucleic acid" includes a plurality of nucleic acids, including mixtures thereof. Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the or method being employed to determine the value.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, a "disruption" or "alteration" of a gene refers to the elimination or reduction of expression of one or more gene products encoded by the subject gene in a cell, compared to the level of expression of the gene product in the absence of the alteration. Exemplary gene products include mRNA and protein products encoded by the gene. Alteration in some cases is transient or reversible and in other cases is permanent. Alteration in some cases is of a functional or full length protein or mRNA, despite the fact that a truncated or non-functional product may be produced. In some embodiments herein, gene activity or function, as opposed to expression, is disrupted. Gene disruption or alteration is generally induced by artificial methods, i.e., by addition or introduction of a compound, molecule, complex, or composition, and/or by alteration of nucleic acid of or associated with the gene, such as at the DNA level. Exemplary methods for gene alteration include gene silencing, knockdown, knockout, and/or gene alteration techniques, such as gene editing. Examples include antisense technology, such as RNAi, siRNA, shRNA, and/or ribozymes, which generally result in transient reduction of expression, as well as gene editing techniques that result in targeted gene inactivation or alteration, e.g., by induction of breaks and/or homologous recombination. Examples include insertions, mutations, and/or deletions. The disruptions or alterations typically result in the repression and/or complete absence of expression of a normal or "wild type" product encoded by the gene. Exemplary of such gene disruptions or alterations are insertions, frameshift and missense mutations, deletions, knock-in, and knock-out of the gene or part of the gene, including deletions of the entire gene. Such alterations can occur in the coding region, e.g., in one or more exons, resulting in the inability to produce a full-length product, functional product, or any product, such as by insertion of a stop codon. Such alterations may also occur by alterations in the promoter or enhancer or other region affecting activation of transcription, so as to prevent transcription of the gene. Gene disruptions or alterations include gene targeting, including targeted gene inactivation by homologous recombination.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "subject," as used herein, generally refers to an individual in need of treatment. The subject can be any animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals. The subject can be a patient, e.g., have or be suspected of having a disease (that may be referred to as a medical condition), such as one or more cancers. The subject may be undergoing or having undergone cancer treatment. The term "individual" may be used interchangeably, in at least some embodiments. The "subject" or "individual", as used herein, may or may not be housed in a medical facility and may be treated as an outpatient of a medical facility. The individual may be receiving one or more medical compositions via the internet. An individual may comprise any age of a human or non-human animal and therefore includes both adult and juveniles (e.g., children) and infants and includes in utero individuals. The individual may be of any gender or race or ethnicity.

"Treating" or treatment of a disease or condition refers to executing a protocol, which may include administering one or more drugs to a patient, in an effort to alleviate signs or symptoms of the disease, including cancer. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, a reduction in the size of a tumor, a reduction in the invasiveness of a tumor, reduction in the growth rate of the cancer, prevention of metastasis, or delay in onset of metastasis. Treatment of cancer may also refer to prolonging survival of a subject with cancer.

II. Embodiments of the Disclosure

The present disclosure concerns methods and compositions for effective cancer therapy, including cancer therapy that avoids severe effects for the treated individual. In particular embodiments, the therapy comprises modification of immune cells, including in an ex vivo manner, and administration of the modified immune cells to an individual with cancer. The immune cells in particular embodiments are of a specific type of T cells, such as Tregs, and their modification is such that the standard function of the Tregs is not deleteriously impacted.

Particular embodiments of the present disclosure encompass SRC-3 as a key target in immune cells, including at least Tregs. With respect to Tregs, the specific compartment-specific disruption leads to tumor eradication at least in a breast cancer syngeneic tumor model, as shown herein. A key difference that differentiates the present strategy of disrupting SRC-3 in Tregs from other immune checkpoint inhibitors is that SRC3 is a nuclear protein, and the modifications in the present disclosure modulate the function of Tregs without losing all activity for the Tregs, which in other cases could result in severe side effects. Furthermore, the present disclosure establishes an approach to specifically ablate SRC3 ex vivo in T cells using CRISPR-based gene targeting. In particular embodiments applied to human CD4+ lymphocytes, for example, the present disclosure provides methods for adoptive T cell/Treg-based therapeutics for the treatment of cancers.

III. Immune Cells

In the present disclosure, immune cells are modified to disrupt expression of endogenous SRC-3 that then allows the cells to be effective for treating cancer in a recipient individual for the cells. Although the immune cells may be of any kind, in specific embodiments they are T cells of any kind, including at least Tregs and B cells.

Embodiments of the present disclosure include modifications of T cells, including Tregs, in which the modification still allows the T cells to perform their desired functions (for Tregs, to control the immune response to self and foreign particles (antigens)). Therefore, the methods and compositions encompassed herein provide cancer therapy that has a reduced risk of toxicity compared to other therapies with modified T cells, including modified T regulatory cells.

Any type of T cell may be utilized in methods and compositions of the disclosure. The term "T cell" refers to T lymphocytes, and includes, but is not limited to, CD4+ T cells, CD8+ T cells, γ:δ+ T cells, or NK T cells. CD4+ T cells include TH0, TH1 and TH2 cells, as well as regulatory T cells (Treg). There are at least three types of regulatory T cells: CD4+CD25+ Treg, CD25 TH3 Treg, and CD25 TR1 Treg. "Cytotoxic T cell" refers to a T cell that can kill another cell. The majority of cytotoxic T cells are CD8+ MHC class I-restricted T cells, however some cytotoxic T cells are CD4+. In particular embodiments, the T cell of the present disclosure is CD4+.

Any T cells utilized herein may be selected for one or more specific markers and/or may be selected against one or more specific markers. Any selection steps may occur by positive selection or negative selection, or both. In particular embodiments, the Tregs are CD4+, CD25+, and/or FOXP3+. In specific cases, the Tregs are CD4+, CD25+, and FOXP3+. In some embodiments, the Tregs are CTL-associated protein 4 (CTLA4)+, C—C chemokine receptor type 7 (CCR7)+, and/or CD62 antigen ligand (CD62L)+. Also included herein are Tregs that through disruption of the SRC-3 gene subsequently cease to express FOXP3, CD25 and/or CD4+.

In some embodiments, CD4+ immune cells, including CD4+ T cells, are targeted with methods and compositions of the disclosure to disrupt expression of SRC-3, and in at least some cases Tregs may be further selected therefrom to be used as the therapeutic cells. In alternative cases, a variety of CD4+ cells are modified and collectively used as the therapeutic cells without a further step of isolating Tregs.

In cases wherein T cells are utilized, the source of the T cells may be of any suitable source, including the spleen, bone marrow, blood, plasma, or a combination thereof. In some cases, the T cells are obtained commercially. In any case, the T cells may be autologous with respect to a recipient individual or allogeneic or syngeneic with respect to a recipient individual. The T cells may be manipulated prior to the step of engineering the cells to have the disruption of SRC-3. In some cases, the cells are processed from a source, such as to remove undesired constituents. The cells may be exposed to one or more compositions that enhance its activity in an individual prior to use therein, such as one or more agents that target SRC-3, or other compositions, such as one or more cytokines and/or one or more growth factors. The cells may be exposed to one or more agents that target SRC-3 prior to, during, and/or subsequent to modification steps to disrupt expression of SRC-3.

IV. Modification of Gene Expression

In particular embodiments, the immune cells of the present disclosure are modified to have altered expression of SRC-3, and such an engineering of the cells may occur by any suitable method. The engineered cells are genetically modified to lack expression or have reduced expression of endogenous SRC-3 in the cells. The reduction in expression may be to a level that it is not detectable by standard methods in the art.

In some embodiments, the altered gene expression is carried out by effecting a disruption in the gene, such as a knock-out, insertion, missense or frameshift mutation, such as biallelic frameshift mutation, deletion of all or part of the gene, e.g., one or more exons or portions therefore, and/or knock-in. For example, the altered gene expression can be effected by sequence-specific or targeted nucleases, including DNA-binding targeted nucleases such as zinc finger nucleases (ZFN) and transcription activator-like effector nucleases (TALENs), and RNA-guided nucleases such as a CRISPR-associated nuclease (Cas), specifically designed to be targeted to the sequence of the SRC-3 gene or a portion thereof.

In some embodiments, the alteration of the expression, activity, and/or function of the gene is carried out by disrupting the gene. In some aspects, the gene is modified so that its expression is reduced by at least at or about 20, 30, or 40%, generally at least at or about 50, 60, 70, 80, 90, 95%, 96%, 97%, 98%, 99%, or more as compared to the expression in the absence of the gene modification or in the absence of the components introduced to effect the modification.

In some embodiments, the alteration is transient or reversible, such that expression of the gene is restored at a later time. In other embodiments, the alteration is not reversible or transient, e.g., is permanent.

In some embodiments, gene alteration is carried out by induction of one or more double-stranded breaks and/or one or more single-stranded breaks in the SRC-3 gene, typically in a targeted manner. In some embodiments, the double-stranded or single-stranded breaks are made by a nuclease, e.g. an endonuclease, such as a gene-targeted nuclease. In some aspects, the breaks are induced in the coding region of the gene, e.g. in an SRC-3 exon. For example, in some embodiments, the induction occurs near the N-terminal portion of the SRC-3 coding region, e.g. in the first exon, in the second exon, or in a subsequent exon.

In some aspects, the double-stranded or single-stranded breaks undergo repair via a cellular repair process, such as by non-homologous end-joining (NHEJ) or homology-directed repair (HDR). In some aspects, the repair process is error-prone and results in disruption of the gene, such as a frameshift mutation, e.g., biallelic frameshift mutation, which can result in complete knockout of the SRC-3 gene. For example, in some aspects, the disruption comprises inducing a deletion, mutation, and/or insertion. In some embodiments, the disruption results in the presence of an early stop codon. In some aspects, the presence of an insertion, deletion, translocation, frameshift mutation, and/ or a premature stop codon results in disruption of the expression, activity, and/or function of the gene.

Any agent(s) for disrupting expression of SRC-3 may be delivered to the recipient cells, such as immune cells that includes T cells of any kind, including Tregs, and in any manner that is suitable. In particular embodiments, the agent(s) may be delivered by nucleofection of any kind, lipofectin, electroporation of any kind, cationic polymers, non-viral vectors (such as plasmids), viral vectors (including adenoviral vectors, retroviral vectors, lentiviral vectors, or adeno-associated viral vectors), cycloamylose-based carriers, nanoparticles of any kind (including metallic or inorganic or polymeric nanoparticles produced using PLGA/ PLA or DODAP-based), lipopolyplexes, and so forth.

In some embodiments, gene alteration is achieved using antisense techniques, such as by RNA interference (RNAi), short interfering RNA (siRNA), short hairpin (shRNA), and/or ribozymes used to selectively suppress or repress expression of the gene. siRNA technology is RNAi that employs a double-stranded RNA molecule having a sequence homologous with the nucleotide sequence of mRNA that is transcribed from the gene, and a sequence complementary with the nucleotide sequence. siRNA generally is homologous/complementary with one region of mRNA that is transcribed from the gene, or may be siRNA including a plurality of RNA molecules that are homologous/complementary with different regions. In some aspects, the siRNA is comprised in a polycistronic construct.

Examples for modifying the cells to have disruption of expression of SRC-3 are as follows:

A. ZFPs and ZFNs

In some embodiments, the DNA-targeting molecule that targets SRC-3 includes a DNA-binding protein such as one or more zinc finger proteins (ZFP) or transcription activator-like proteins (TAL), fused to an effector protein such as an endonuclease. Examples include ZFNs, TALEs, and TALENs.

In some embodiments, the DNA-targeting molecule comprises one or more zinc-finger proteins (ZFPs) or domains thereof that bind to DNA in a sequence-specific manner A ZFP or domain thereof is a protein or domain within a larger protein that binds DNA in a sequence-specific manner through one or more zinc fingers, regions of amino acid sequence within the binding domain whose structure is stabilized through coordination of a zinc ion. The term zinc finger DNA binding protein is often abbreviated as zinc finger protein or ZFP. Among the ZFPs are artificial ZFP domains targeting specific DNA sequences, typically 9-18 nucleotides long, generated by assembly of individual fingers.

ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice.

In some embodiments, the DNA-targeting molecule is or comprises a zinc-finger DNA binding domain fused to a DNA cleavage domain to form a zinc-finger nuclease (ZFN). In some embodiments, fusion proteins comprise the cleavage domain (or cleavage half-domain) from at least one Type 1iS restriction enzyme and one or more zinc finger binding domains, which may or may not be engineered. In some embodiments, the cleavage domain is from the Type 1iS restriction endonuclease Fok I. Fok I generally catalyzes double-stranded cleavage of DNA, at 9 nucleotides from its recognition site on one strand and 13 nucleotides from its recognition site on the other.

Many gene-specific engineered zinc fingers are available commercially. For example, Sangamo Biosciences (Richmond, Calif., USA) has developed a platform (CompoZr) for zinc-finger construction in partnership with Sigma-Aldrich (St. Louis, Mo., USA), allowing investigators to bypass zinc-finger construction and validation altogether, and provides specifically targeted zinc fingers for thousands of proteins (Gaj et al., Trends in Biotechnology, 2013, 31(7), 397-405). In some embodiments, commercially available zinc fingers are used or are custom designed. (See, for example, Sigma-Aldrich catalog numbers CSTZFND, CSTZFN, CTil-1KT, and PZD0020).

B. TALs, TALEs and TALENs

In some embodiments, the DNA-targeting molecule for SRC-3 comprises a naturally occurring or engineered (non-naturally occurring) transcription activator-like protein (TAL) DNA binding domain, such as in a transcription activator-like protein effector (TALE) protein, See, e.g., U.S. Patent Publication No. 2011/0301073, incorporated by reference in its entirety herein.

A TALE DNA binding domain or TALE is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Di-residue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NO binds to T and non-canonical (atypical) RVDs are also known. In some embodiments, TALEs may be targeted to any gene by design of TAL arrays with specificity to the target DNA sequence. The target sequence generally begins with a thymidine.

In some embodiments, the molecule is a DNA binding endonuclease, such as a TALE nuclease (TALEN). In some aspects the TALEN is a fusion protein comprising a DNA-binding domain derived from a TALE and a nuclease catalytic domain to cleave a nucleic acid target sequence.

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation or via the so-called microhomology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

In some embodiments, TALE repeats are assembled to specifically target a gene. (Gaj et al., 2013). A library of TALENs targeting 18,740 human protein-coding genes has been constructed (Kim et al., 2013). Custom-designed TALE arrays are commercially available through Cellectis Bioresearch (Paris, France), Transposagen Biopharmaceuticals (Lexington, Ky., USA), and Life Technologies (Grand Island, N.Y., USA). Specifically, TALENs that target CD38 are commercially available (See Gencopoeia, catalog numbers HTN222870-1, HTN222870-2, and HTN222870-3). Exemplary molecules are described, e.g., in U.S. Patent Publication Nos. US 2014/0120622, and 2013/0315884.

In some embodiments the TALEN s are introduced as trans genes encoded by one or more plasmid vectors. In some aspects, the plasmid vector can contain a selection marker which provides for identification and/or selection of cells which received said vector.

C. RGENs (CRISPR/Cas Systems)

In some embodiments, the alteration of the SRC-3 gene is carried out using one or more DNA-binding nucleic acids, such as alteration via an RNA-guided endonuclease (RGEN). For example, the alteration can be carried out using clustered regularly interspaced short palindromic repeats (CRISPR) and CRISPR-associated (Cas) proteins. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The CRISPR system can induce double stranded breaks (DSBs) at the SRC-3 target site, followed by disruptions or alterations as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

The target sequence for SRC-3 may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2.

The CRISPR enzyme can be Cas9 (e.g., from S. pyogenes or S. pneumonia). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US 20110059502, incorporated herein by reference.

V. Methods of Use

In some embodiments, the present disclosure provides methods for cancer treatment that employs immunotherapy, comprising administering an effective amount of SRC-3-disrupted immune cells of the present disclosure. In one embodiment, methods are encompassed herein for treating, delaying progression of, delaying onset of, or reducing the risk of getting cancer in an individual by administering to the individual an effective amount the SRC-3-disrupted cell therapy. The present methods may be applied for the treatment of solid cancers or hematologic cancers. In specific embodiments, the cancer is SRC-3 positive. The cancer may be primary, metastatic, refractory to therapy, and so forth. The cancer may be of any type and of any stage. The individual may be at risk for cancer, including over the general population, and the individual at risk for cancer may be so because of a personal or family history, because the individual is a tobacco user, is obese, consumes excessive alcohol, has some types of viral infections, such as human papillomavirus (HPV), has exposure to one or more carcinogens, or has had excessive exposure to radiation, including ultraviolet radiation from the sun. An amount may be considered excessive when it is greater than the average individual of a population.

Tumors for which the disclosed treatment methods are useful include any malignant cell type, such as those found in a solid tumor or a hematological tumor. Exemplary solid tumors can include, but are not limited to, a tumor of an organ selected from the group consisting of breast, ovary, pancreas, colon, cecum, stomach, brain, head, neck, kidney, larynx, sarcoma, lung, bladder, melanoma, prostate, gastric tissue, and endometrium. Exemplary hematological tumors include tumors of the bone marrow, T or B cell malignancies, leukemias, lymphomas, blastomas, myelomas, and the like. Particular examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma;

ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

In certain embodiments of the present disclosure, immune cells are delivered to an individual in need thereof, such as an individual that has cancer or is suspected of having cancer. The cells then enhance the individual's immune system to attack the respective cancer. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days. In some cases, the duration between administrations is 1-24 hours, 1-7 days, 1-4 weeks, 1-12 months, or more, or any range derivable there between.

In some embodiments, the subject can be administered nonmyeloablative lymphodepleting chemotherapy prior to the immune cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m2 fludarabine is administered for five days.

In certain embodiments, one or more growth factors and/or one or more cytokines that promotes the growth and activation of the immune cells is administered to the subject either concomitantly with the immune cells or subsequently to the immune cells. The immune cell growth factor can be any suitable growth factor that promotes the growth and activation of the immune cells. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of immune cells can be administered by a number of routes, including parenteral administration, for example, intravenous, intraperitoneal, intramuscular, intrasternal, or intraarticular injection, intranasal, intraarterial, or by infusion.

The therapeutically effective amount of immune cells for use in adoptive cell therapy is that amount that achieves a desired effect in a subject being treated. For instance, this can be the amount of immune cells necessary to inhibit growth, or to cause regression of cancer, or improve at least one symptom of cancer.

The immune cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of immune cells will be dependent on the subject being treated, the severity and type of the affliction, and the manner of administration. In some embodiments, doses that could be used in the treatment of human subjects range from at least $3.8 \times 10^4$, at least $3.8 \times 10^5$, at least $3.8 \times 10^6$, at least $3.8 \times 10^7$, at least $3.8 \times 10^8$, at least $3.8 \times 10^9$, or at least $3.8 \times 10^{10}$ immune cells/m2. In a certain embodiment, the dose used in the treatment of human subjects ranges from about $3.8 \times 10^9$ to about $3.8 \times 10^{10}$ immune cells/m2. In additional embodiments, a therapeutically effective amount of immune cells can vary from about $5 \times 10^6$ cells per kg body weight to about $7.5 \times 10^8$ cells per kg body weight, such as about $2 \times 10^7$ cells to about $5 \times 10^8$ cells per kg body weight, or about $5 \times 10^7$ cells to about $2 \times 10^8$ cells per kg body weight. The exact amount of immune cells is readily determined by one of skill in the art based on the age, weight, sex, and physiological condition of the subject. Effective doses can be extrapolated from dose-response curves derived from in vitro or animal model test systems.

The immune cells may be administered in combination with one or more other therapeutic agents for the treatment of the cancer. Combination therapies can include, but are not limited to, one or more anti-tumor agents or a vaccine. In specific cases, chemotherapeutic agents (e.g., Methotrexate, Treosulfan, Busulfan); irradiation; or chemokines, interleukins or their inhibitors (e.g., BAFF, IL-2, anti-IL-2R, IL-4, JAK kinase inhibitors) can be administered in addition to the immune cells. Such additional pharmaceutical agents can be administered before, during, or after administration of the immune cells, depending on the desired effect. This administration of the cells and the one or more additional anti-cancer agents can be by the same route or by different routes, and either at the same site or at a different site.

VI. Pharmaceutical Compositions

Provided herein are pharmaceutical compositions and formulations comprising immune cells (e.g., SRC-3 disrupted immune cells, including T cells such as Treg cells) and a pharmaceutically acceptable carrier. In some embodiments, there are compositions comprising: (a) any of the immune cells encompassed herein; and (b) one or more agents that target SRC-3. In such cases, (a) and (b) may or may not be in the same formulation and may or may not be configured to be delivered by the same route of administration.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutralactive hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

VII. Combination Therapies

In certain embodiments, the compositions and methods of the present embodiments involve an immune cell population in combination with at least one additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, protein therapy, or a combination of the foregoing. The additional therapy may be in the form of adjuvant or neoadjuvant therapy. The additional therapy may be one or more agents that target SRC-3, such as antibodies of any kind, small molecule inhibitors, nucleic acids, proteins, or a combination thereof.

In some embodiments, the additional therapy is the administration of small molecule inhibitor of SRC-3 or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

An immune cell therapy may be administered before, during, after, or in various combinations relative to an additional cancer therapy. The administrations may be in intervals ranging from concurrently to minutes to hours to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient.

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gamma1I and calicheamicin omega1I); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin; procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that additional immunotherapies to those encompassed herein may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach, merely as examples.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAGS), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4. Another immune checkpoint that can be targeted in the methods provided herein is the cytotoxic T-lymphocyte-associated protein 4 (CTLA-4), also known as CD152. In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

VIII. Engineered B Cells and Methods of Use

In particular embodiments, the immune cells that are engineered to have disruption of SRC-3 include B cells. In particular embodiments, SRC-3-disrupted B cells are utilized for any medical condition for which the B cells would be effective, but in specific embodiments the modified B cells are utilized for treatment of one or more inflammatory diseases or treatment of cancer of any kind, including at least B cell lymphomas and those cancers listed elsewhere herein, for example.

In certain embodiments, B cells are obtained either commercially or from the individual in need of the treatment. The B cells may be obtained from a healthy individual for allogeneic purposes. The B cells may be engineered ex vivo by standard methods to disrupt expression of endogenous SRC-3 in the B cells. In some cases, the engineered B cells are exposed to one or more agents including TGF-□ or tumor-specific antigens that facilitate efficacy of the B cells once administered to the individual in need.

In particular embodiments, the engineered B cells lacking expression of SRC-3 or having reduced expression of SRC-3 compared to non-engineered B cells are administered in an effective amount to an individual having or at risk for having one or more inflammatory diseases. Although the inflammatory disease may be of any kind, in specific embodiments the disease is allergy, asthma, autoimmune diseases, coeliac disease, glomerulonephritis, hepatitis, inflammatory bowel disease, preperfusion injury, transplant rejection, ankylosing spondylitis (AS), gout; myositis, rheumatoid arthritis, scleroderma, Sjogren's Syndrome, systemic lupus Erythematosus (SLE, Lupus), pelvic inflammatory disease, or vasculitis, merely as examples. The B cell treatment may reduce or delay the severity of the disease, delay the onset of the disease, improve one or more symptoms of the disease, and so forth.

IX. Articles of Manufacture or Kits

An article of manufacture or a kit is provided comprising immune cells is also provided herein. The immune cells may be T cells, such as Treg cells. The kit may comprise the cells without having the SRC-3 disruption, one or more reagents to produce the SRC-3 disruption (including, e.g., nucleic acids and proteins that facilitate knockout or knockdown of SRC-3 specifically), cells that have the SRC-3 disruption, one or more agents that target SRC-3, buffers, salts, directions for use, or a combination thereof. In specific embodiments, the kit comprises CRISPR reagents for targeting SRC-3, T regulatory cells, or both.

The article of manufacture or kit can further comprise a package insert comprising instructions for using the immune cells to treat or delay progression of cancer in an individual. Any of the immune cells described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or a nickel-molybdenum alloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

EXAMPLES

The following examples are included to demonstrate preferred embodiments of the disclosure. It should be appreciated by those of skill in the art that the techniques disclosed in the examples that follow represent techniques discovered by the inventors to function well in the practice of the methods and compositions of the disclosure, and thus can be considered to constitute particular modes for its practice. However, those of skill in the art should, in light of the present disclosure, appreciate that many changes can be made in the specific embodiments that are disclosed and still obtain a like or similar result without departing from the spirit and scope of the disclosure.

Example 1

SRC-3 Controls Immune Cell Populations

Figures 2A, 2B:
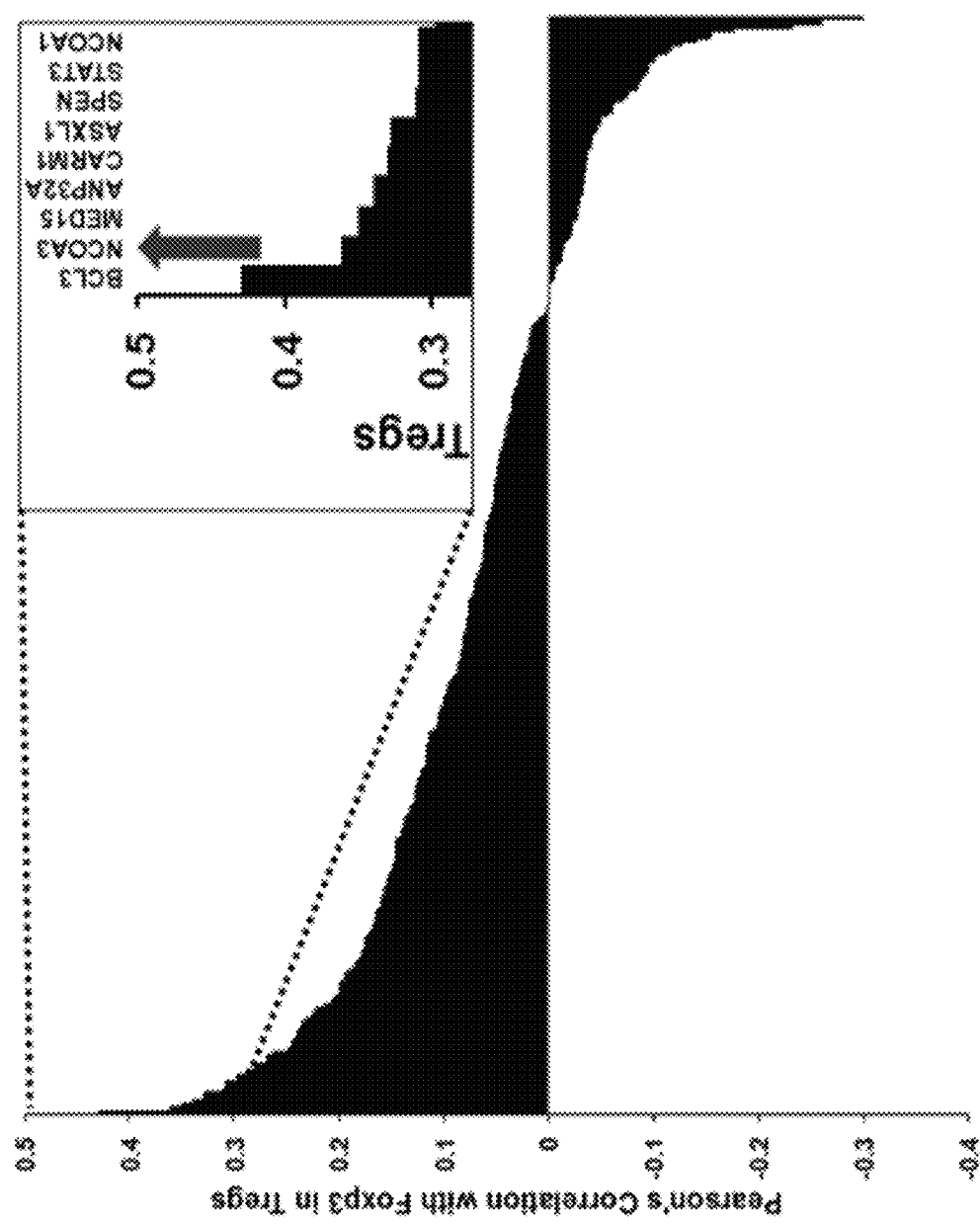
FIGS. 2A-2B: SRC-3 expression is highly enriched and correlated with Foxp3 in regulatory T cells (Tregs).
Figure 3A:
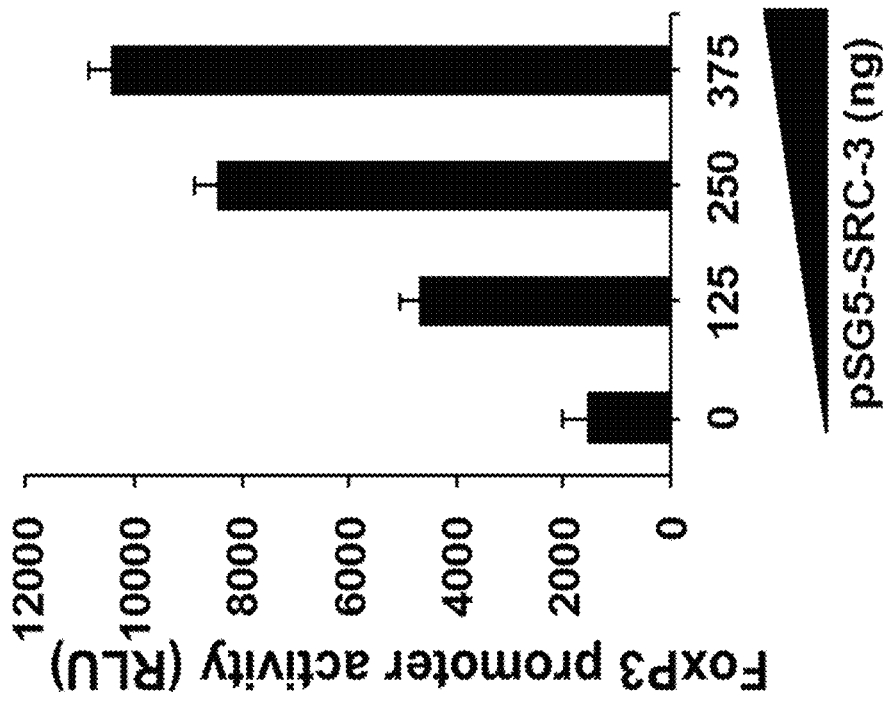
FIGS. 3A-3B: SRC-3 regulates FOXP3 expression in human Tregs.
Figure 3B:
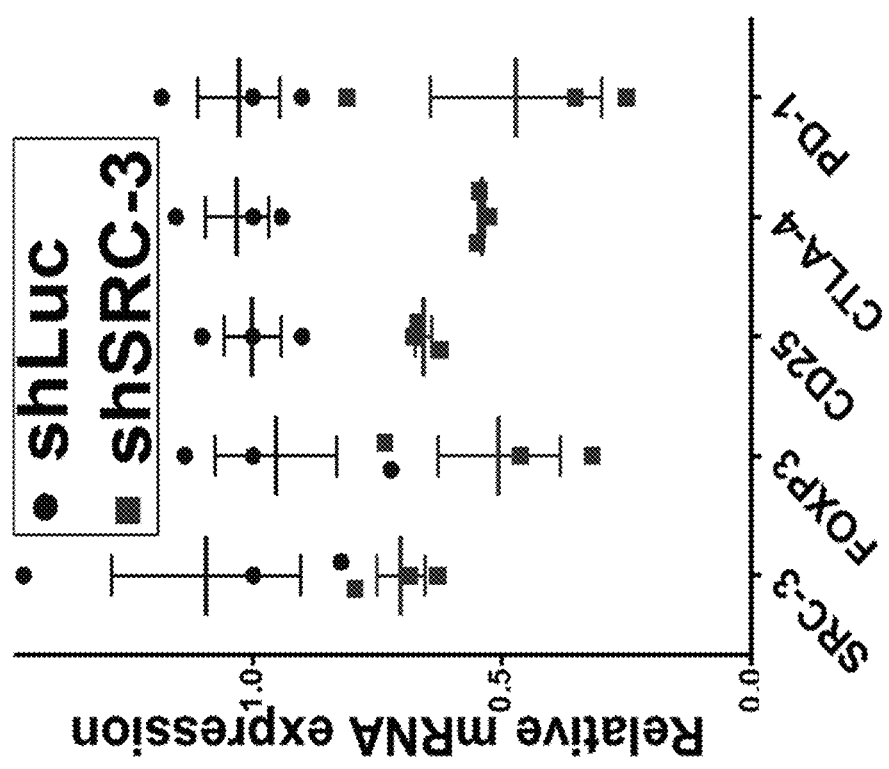
Figure 5:
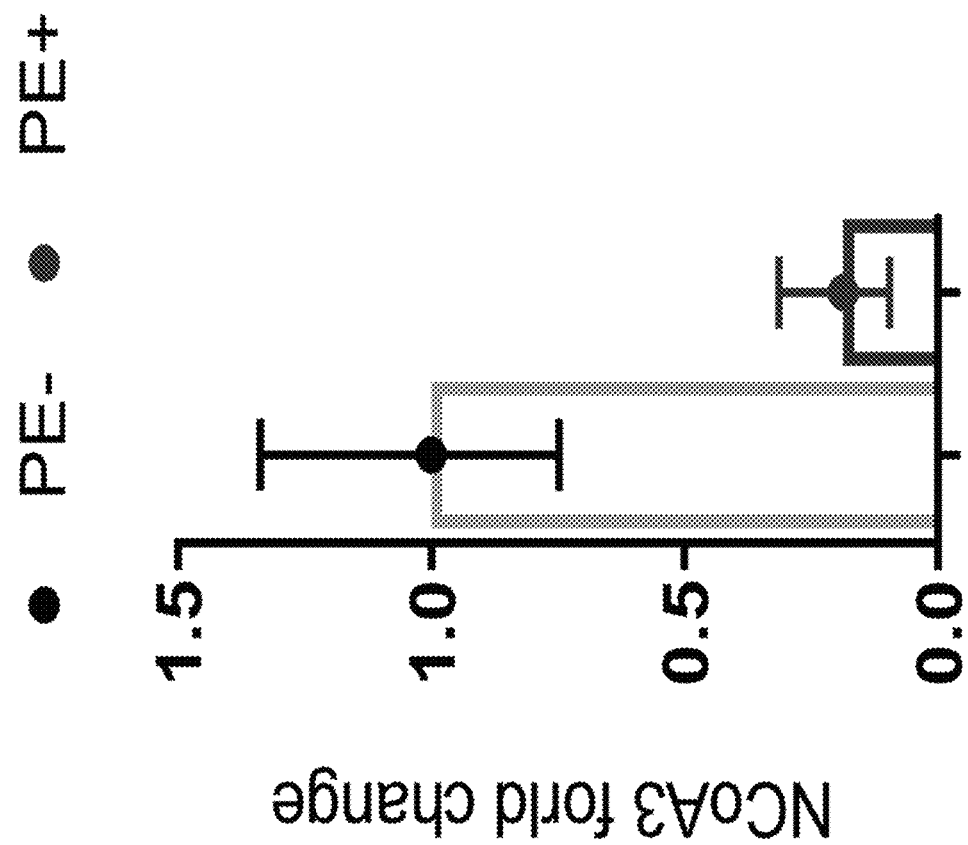
FIG. 5: Quantitation of SRC-3 (NcoA3) mRNA in bulk T lymphocytes following CRISPR-based targeting of the SRC-3 gene. The following primers were used for RT-qPCR assay performed above. NCoA3 primers (probe 103): Left: AAG ACT CTT TAG GAC CGC TTT TAC T (SEQ ID NO:1). Right: ACA CTG CGC CAT GGT TAA T (SEQ ID NO:2). GAPDH primers (probe 52): Left: GGG TTC CTA TAA ATA CGG ACT GC (SEQ ID NO:3). Right: CCA TTT TGT CTA CGG GAC GA (SEQ ID NO:4). (PE−)—non-targeted cells; (PE+) SRC-3 gene targeted cells.

Although the cell-autonomous, oncogenic functions of SRC-3 (gene name: NCOA3) in the breast cancer cell have been well established (1-9), the role(s) of SRC-3 expressed in immune cells are largely unknown. Genetic deletion of the Src-3 gene in mice results in the expansion of the lymphoid lineage, leading to increased numbers of CD4+ and CD8+ T cells as well as B lymphocytes (first reported in (11) and recent data recapitulating this observation are shown in FIG. 1). There were elevated levels of several cytokines, including CXCL2, IL2, IL1α and β, CCL2, and GCSF, in the peripheral blood of Src-3 KO mice (data not shown). These findings uncover immunosuppressive functions of SRC-3, highlighting it as a novel transcriptional immune checkpoint regulator and strongly suggest that pharmacological inhibition of SRC-3 in immune cells can bolster their ability to attack cancer cells. However, the exact immune cell population where SRC-3 exerts this role remained to be defined. Gene expression analysis of public datasets revealed that SRC-3 expression is very high in Treg cells and is correlated with Foxp3 expression (FIG. 2). Amongst 296 curated coregulators in the Nuclear Receptor Signaling Atlas (NURSA), NCOA3 (Src-3) was the second most correlated coactivator with Foxp3 expression in Tregs (FIG. 3).

Example 2

Genetic Disruption of SRC-3 in Tregs Promotes Robust Breast Cancer Tumor Clearance Given the previously reported data showing that SRC-3−/− mice have a lymphoproliferative phenotype and that disruption of SRC-3 expression in Tregs results in reduced expression of immunosuppressive proteins in this cell type, the inventors characterized SRC-3 as an immune checkpoint modulatory protein specifically in the 'Treg compartment' using a mouse genetic model system. The inventors back-crossed SRC-3flox/flox mice for 10 generations into a pure C57BL/6J background and then crossed this mouse with a Foxp3:EGFP-Cre-ERT2 mouse that is already on a C57BL/6J background to create Treg:SRC-3KO mice.

Tamoxifen treatment will activate the Cre, resulting in the disruption of the SRC-3 gene specifically in Tregs. Using this genetically engineered mouse model system, the effects of SRC-3 gene disruption were tested in a wide range of immunocompetent, syngeneic tumor cell lines that are compatible with the C57BL/6J background, including the E0771 mouse mammary gland tumor line shown below. E0771 tumors are particularly aggressive and it is well known that it is difficult to control tumor growth in this model system. However, in host mice where SRC-3 was disrupted specifically in Tregs, the tumors were essentially eradicated, while in wild-type host animals, tumors rapidly grew to a large size (FIG. 4).

The results from this study powerfully demonstrate that SRC-3 is a newly discovered and key immune checkpoint regulatory target. Another unexpected and important outcome from this animal model experiment was that the animals appeared to be healthy, with normal size spleens without any significant changes in body weight or activity. This is in contrast to Foxp3-mutated scurfy mice that have a severe autoimmune phenotype and die at an early age. In a specific embodiment, the Treg:SRC-3KO mice differ from scurfy mice because the genetic disruption of SRC-3 in Foxp3 cells only disrupts a subset of the Tregs' immunosuppressive activities. Existing immune checkpoint modulator drugs in the clinic possess strong, dose-limiting and life-threatening side effect profiles. Therefore, in specific embodiments inhibition of only certain aspects of Treg biology with SRC-3 SMIs makes it possible to target only their tumor-related immunosuppression without generally over-stimulating unwanted immune system events in other tissues.

Example 3

CRISPR-Based Targeting of SRC-3 in Tregs

The genetically engineered mouse model demonstrates that specifically targeting SRC-3 in Tregs results in the eradication of an aggressive mammary gland carcinoma. In order to translate this finding into a clinically translatable therapeutic treatment, the inventors have developed a method to target the SRC-3 gene in mouse immune cells using a CRISPR-based approach described below. In particular embodiments, the genetically altered cells are used as a source of Tcells/Tregs for adoptive therapy to eliminate breast tumors in syngeneic mouse model systems. This process is adaptable to human CD4+ cells (for example) that are useful to treat human patients with breast or other cancers.

Spleens were harvested from a 12 weeks old male C57BL/6 mice. A single cell suspension of splenocytes was prepared by mashing the spleens through a 40 μm cell strainer using the plunger end of a syringe. The splenocyte suspension was placed in a conical tube, centrifuged (1500 rpm, 5 min) and the red cell pellet was subjected to RBC removal using RBC removal buffer (Sigma R 7757), resulting in a beige lymphocytes pellet. The lymphocytes were plated in a CD3 coated plate using full RPMI media (L-glu, FBS, antibiotics) supplemented with CD28/IL2/MeSH. After three days of culture, cell viability was assessed (80%) and bulk lymphocytes were subjected to CD4 enrichment using a Miltenyi CD4 enrichment kit (130-104-545). Enriched CD4 cells (40M) were plated for an additional two days in the above described conditions resulting in expansion of the cell population to more than 100 million cells.

Nucleofection: The enriched and expanded population of CD4 cells was subjected to nucleofection with a Cas9-NCoA3 guide RNA (gRNA) ribonucleoprotein (RNP) using a Lonza 4D nucleofector and primary cells nucleofection kit (Lonza V4XP-3024). The RNP was prepared by mixing fluorescently labeled trcrRNA (IDT #1075928) with crRNA (IDT) at a 1:1 ratio (11.25 μl TrcrRNA-ATTO 550 with three distinct crRNAs—3.75 μl each). gRNA (comprised of trcrRNA+crRNA) was incubated at 37° C. for 15 min. Then the gRNA (concentration 50 μM) was mixed with Cas9 protein (IDT #1081059, concentration 60 μM) at a ratio of 3:1, resulting in a 15 μM RNP with an excess of the gRNA component. The RNP was incubated at 37° C. for 15 min and then mixed with the nucleofection buffer at a 1:5 ratio. Thirteen nucleofection reactions were prepared—each reaction contained 8 to 10 million CD4 cells and 130 μl RNP-nucleofection buffer mix (final concentration of the RNP is 3.5 μM with a 3 fold excess of the gRNA component). The nucleofection was performed in the 4D nucleofector by subjecting each nucleocuvvete to the manufacturers' EN138 pulse program.

After the nucleofection, the cells were supplied with culture media and transferred to a culture dish covered with CD3. After an overnight recovery, the cells were sorted by flow cytometry to allow separation of the nucleofected population (by tracking the fluorescently labeled gRNA). The sorted populations (positive and negative) were cultured for five days to allow for the genetic editing to take place and for protein turnover and cell expansion to occur. Subsequently, total RNA was isolated from these cells, followed by two step RT-qPCR to test for the disruption of SRC-3 (gene symbol Ncoa3) expression.

These results demonstrate that CRISPR-based disruption of SRC-3 in T lymphocytes is robust and produces a high yield of viable, expandable cells for further downstream applications, such as adoptive T cell transfer.

The data strongly implicates SRC-3 as a key target in Tregs, and its specific disruption in this cellular compartment leads to tumor eradication in a breast cancer syngeneic tumor model. The present strategy of disrupting SRC-3 in Tregs differentiates from other immune checkpoint inhibitors, because SRC-3 is a nuclear protein that modulates the function of Tregs in a way that promotes tumor eradication without entirely obliterating their function, which is associated with potentially severe side-effects. The present disclosure provides an approach to specifically ablate SRC-3 ex vivo in T cells obtained from mice using CRISPR-based gene targeting. When applied using human CD4+ lymphocytes, this method has a clear, translatable potential as an adoptive T cell/Treg based therapeutic for the treatment of human cancers.

Example 4

Adoptive SRC-3 KO Treg Cell Transfer to Breast Tumor-Bearing Mice

Given the previously reported data showing that SRC-3−/− mice have a lymphoproliferative phenotype and that disruption of SRC-3 expression in Tregs results in reduced expression of immunosuppressive proteins in this cell type, the inventors characterized SRC-3 as an immune checkpoint modulatory protein specifically in the 'Treg compartment' using a mouse genetic model system. The inventors backcrossed SRC-3flox/flox mice for 10 generations into a pure C57BL/6J background and then crossed this mouse with a Foxp3:EGFP-Cre-ERT2 mouse already on a C57BL/6J background to create Treg:SRC-3KO C57BL/6J mice.

Tamoxifen treatment activates the Cre, resulting in disruption of the SRC-3 gene specifically in Treg cells. This genetically engineered mouse model system was used to produce SRC-3 knockout (KO) Treg cells isolated from spleens removed from the SRC-3 KO Treg animals. Approximately 1.6 million SRC-3 KO Treg cells were isolated from a spleen, and the isolated SRC-3 KO Treg cells were 92% viable. As a control, Treg cells (approximately 1.9 million) were also isolated from a spleen removed from a SRC-3 flox/flox (SRC-3$^{F/F}$) mouse, and the isolated control cells were 93% viable.

Figure 6:
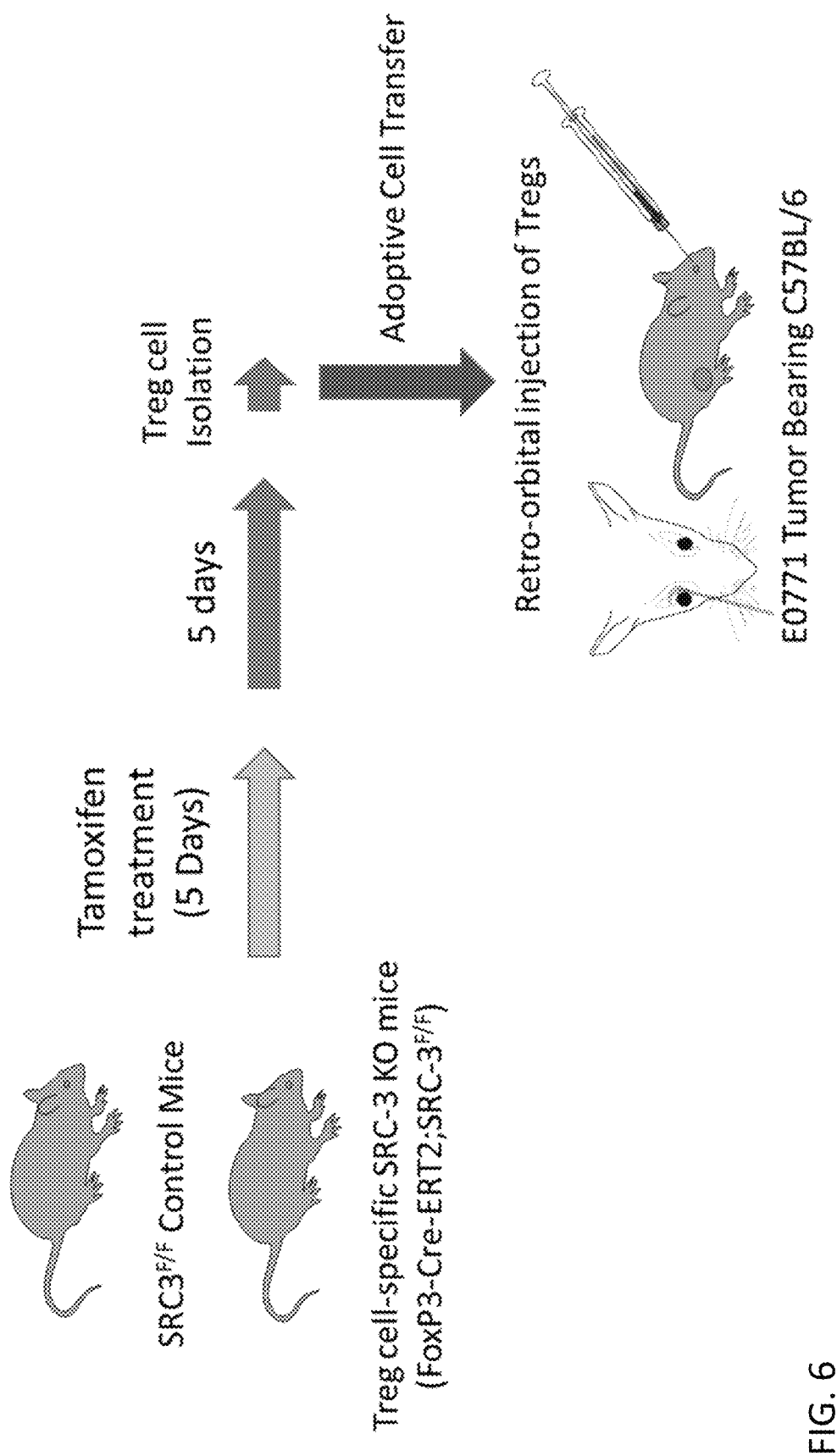
FIG. 6: Experimental design of adoptive SRC-3 KO Treg mouse tumor model.
Figure 7A:
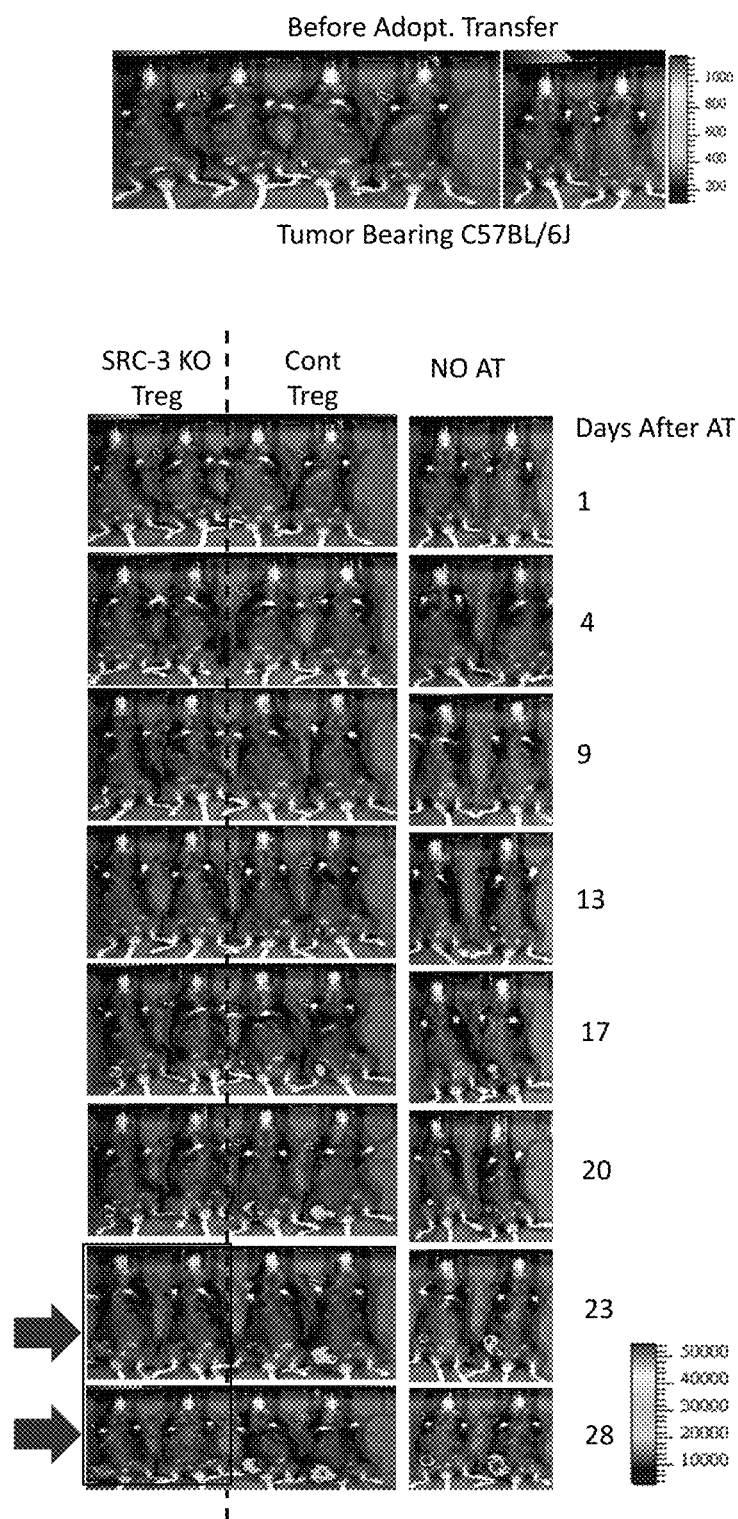
FIGS. 7A-7B: Adoptive transfer of SRC-3 KO Treg cells eliminates E0771 tumors.
Figure 7B:
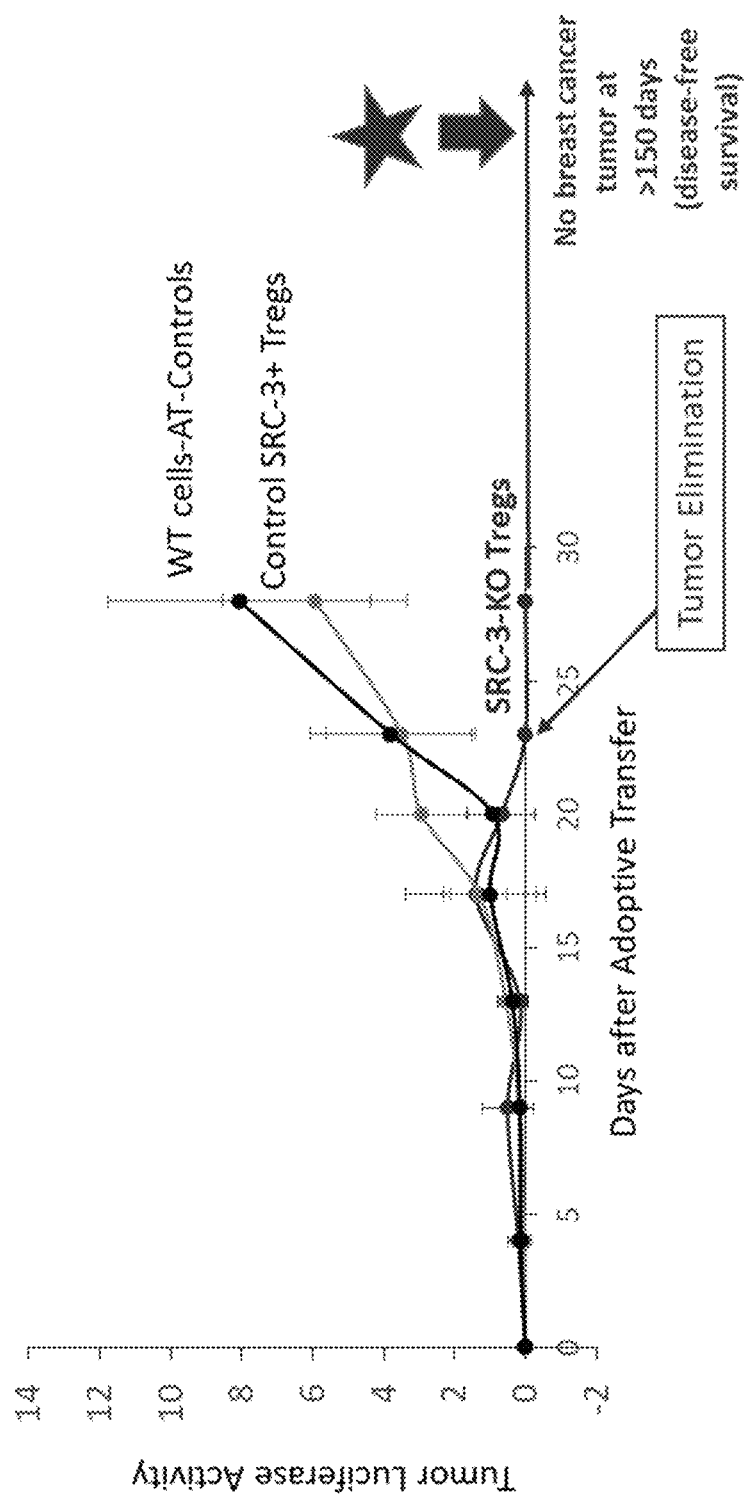

The effects of the isolated SRC-3 KO Treg cells were tested in C57BL/6J mice bearing tumors derived from E0771 cells, which are derived from a murine mammary cancer cell line originally isolated from a spontaneous tumor in a C57BL/6 mouse (FIG. 6). E0771 tumors are particularly aggressive and it is difficult to suppress E0771 tumor growth in immune-intact C57BL/6J mice. However, the E0771 tumors were essentially eradicated in mice treated with isolated SRC-3 KO Treg cells (0.9 million cells) compared to the growth of E0771 tumors in C57BL/6J mice without adoptive Treg cell transfer (No AT). In contrast, transfer of 0.9 million Treg cells from SRC-3$^{F/F}$ control mice (Cont Treg, Control SRC-3+ Tregs) did not suppress the growth of E0771 cells compared to the growth of E0771 tumors in C57BL/6J mice without adoptive Treg cell transfer (FIG. 7). Furthermore, adoptive SRC-3 KO Treg cell transfer did not cause apparent toxicity, and animals receiving the SRC-3 KO Treg cells remained reproductively fertile (data not shown).

The results from this study demonstrate that adoptive transfer of SRC-3 KO Treg cells is useful for cancer treatment, and, in specific embodiments, SRC-3 KO Treg cells are used to control and/or eliminate tumor growth.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

1. Geng C, He B, Xu L, Barbieri C E, Eedunuri V K, Chew S A, Zimmermann M, Bond R, Shou J, Li C, Blattner M, Lonard D M, Demichelis F, Coarfa C, Rubin M A, Zhou P, O'Malley B W, Mitsiades N. Prostate cancer-associated mutations in speckle-type POZ protein (SPOP) regulate steroid receptor coactivator 3 protein turnover. Proc Natl Acad Sci USA. 2013; 110(17):6997-7002. doi: 10.1073/pnas.1304502110. PubMed PMID: 23559371; PMCID: PMC3637757.
2. Eedunuri V K, Rajapakshe K, Fiskus W, Geng C, Chew S A, Foley C, Shah S S, Shou J, Mohamed J S, Coarfa C, O'Malley B W, Mitsiades N. miR-137 Targets p160 Steroid Receptor Coactivators SRC1, SRC2, and SRC3 and Inhibits Cell Proliferation. Mol Endocrinol. 2015; 29(8):1170-83. doi: 10.1210/me.2015-1080. PubMed PMID: 26066330; PMCID: PMC4518002.
3. Coarfa C, Fiskus W, Eedunuri V K, Rajapakshe K, Foley C, Chew S A, Shah S S, Geng C, Shou J, Mohamed J S, O'Malley B W, Mitsiades N. Comprehensive proteomic profiling identifies the androgen receptor axis and other signaling pathways as targets of microRNAs suppressed in metastatic prostate cancer. Oncogene. 2016; 35(18): 2345-56. doi: 10.1038/onc.2015.295. PubMed PMID: 26364608; PMCID: PMC5915337.
4. Wang Y, Lonard D M, Yu Y, Chow D C, Palzkill T G, O'Malley B W. Small molecule inhibition of the steroid receptor coactivators, SRC-3 and SRC-1. Mol Endocrinol. 2011; 25(12):2041-53. Epub 2011/11/05. doi: me.2011-1222 [pii] 10.1210/me.2011-1222. PubMed PMID: 22053001; PMCID: 3231837.
5. Tien J C, Liu Z, Liao L, Wang F, Xu Y, Wu Y L, Zhou N, Ittmann M, Xu J. The steroid receptor coactivator-3 is required for the development of castration-resistant prostate cancer. Cancer Res. 2013; 73(13):3997-4008. Epub 2013/05/08. doi: 0008-5472.CAN-12-3929 [pii] 10.1158/0008-5472.CAN-12-3929. PubMed PMID: 23650284; PMCID: 3732785.
6. Zhou H J, Yan J, Luo W, Ayala G, Lin S H, Erdem H, Ittmann M, Tsai S Y, Tsai M J. SRC-3 is required for prostate cancer cell proliferation and survival. Cancer Res. 2005; 65(17):7976-83. Epub 2005/09/06. doi: 65/17/7976 [pii] 10.1158/0008-5472.CAN-04-4076. PubMed PMID: 16140970.
7. Yan J, Yu C T, Ozen M, Ittmann M, Tsai S Y, Tsai M J. Steroid receptor coactivator-3 and activator protein-1 coordinately regulate the transcription of components of the insulin-like growth factor/AKT signaling pathway. Cancer Res. 2006; 66(22):11039-46. Epub 2006/11/17. doi: 66/22/11039 [pii] 10.1158/0008-5472.CAN-06-2442. PubMed PMID: 17108143.
8. Ayala G, Yan J, Li R, Ding Y, Thompson T C, Mims M P, Hayes T G, MacDonnell V, Lynch R G, Frolov A, Miles B J, Wheeler T M, Harper J W, Tsai M J, Ittmann M M, Kadmon D. Bortezomib-mediated inhibition of steroid receptor coactivator-3 degradation leads to activated Akt. Clin Cancer Res. 2008; 14(22):7511-8. Epub 2008/11/18. doi: 14/22/7511 [pii] 10.1158/1078-0432.CCR-08-0839. PubMed PMID: 19010869; PMCID: 2820291.
9. Yan J, Erdem H, Li R, Cai Y, Ayala G, Ittmann M, Yu-Lee L Y, Tsai S Y, Tsai M J. Steroid receptor coactivator-3/AIB1 promotes cell migration and invasiveness through focal adhesion turnover and matrix metalloproteinase expression. Cancer Res. 2008; 68(13):5460-8. Epub 2008/07/03. doi: 68/13/5460 [pii] 10.1158/0008-5472.CAN-08-0955. PubMed PMID: 18593949.
10. Wu C, Orozco C, Boyer J, Leglise M, Goodale J, Batalov S, Hodge C L, Haase J, Janes J, Huss J W, 3rd, Su A I. BioGPS: an extensible and customizable portal for querying and organizing gene annotation resources. Genome Biol. 2009; 10(11):R130. doi: 10.1186/gb-2009-10-11-r130. PubMed PMID: 19919682; PMCID: PMC3091323.
11. Coste A, Antal M C, Chan S, Kastner P, Mark M, O'Malley B W, Auwerx J. Absence of the steroid receptor coactivator-3 induces B-cell lymphoma. EMBO J. 2006; 25(11):2453-64. Epub 2006/05/06. doi: 7601106 [pii] 10.1038/sj.emboj.7601106. PubMed PMID: 16675958; PMCID: 1478181.

12. Vandenbon A, Dinh V H, Mikami N, Kitagawa Y, Teraguchi S, Ohkura N, Sakaguchi S. Immuno-Navigator, a batch-corrected coexpression database, reveals cell type-specific gene networks in the immune system. Proc Natl Acad Sci USA. 2016; 113(17):E2393-402. doi: 10.1073/pnas.1604351113. PubMed PMID: 27078110; PMCID: PMC4855614.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of producing engineered CD4+ T regulatory cells, comprising:
    (a) obtaining CD4+ T regulatory cells (Tregs); and
    (b) exposing the CD4+ Tregs to one or more agents that disrupt expression of endogenous SRC-3 in the Tregs; or
    (a) obtaining immune cells that comprise CD4$^+$ T regulatory cells;
    (b) exposing the immune cells to one or more agents that disrupt expression of endogenous SRC-3 in the immune cells; and
    (c) selecting for CD4+ T regulatory cells.

2. The method of claim 1, wherein the one or more agents that disrupt expression of endogenous SRC-3 in the cells comprises nucleic acid or CRISPR reagents.

3. The method of claim 1, further comprising the step of exposing the CD4+ T regulatory cells or immune cells ex vivo to an effective amount of one or more agents that target SRC-3, wherein the said one or more agents that target SRC-3 are different agents than those in step (b).

4. The method of claim 3, wherein the one or more agents that targets SRC-3 is a small molecule inhibitor, an antibody, a protein, a nucleic acid, or a combination thereof.

5. The method of claim 1, further comprising the step of exposing the cells to one or more agents that target SRC-3 prior to, during, and/or subsequent to step (b), wherein the said one or more agents that target SRC-3 are different agents than those in step (b).

6. The method of claim 5, wherein the one or more agents that targets SRC-3 is a small molecule inhibitor, an antibody, a protein, a nucleic acid, or a combination thereof.

7. The method of claim 1, wherein the Tregs are CD25+ and/or FOXP3+.

* * * * *

SEQUENCE LISTING

```
<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aagactcttt aggaccgctt ttact                                            25

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acactgcgcc atggttaat                                                  19

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggttcctat aaatacggac tgc                                             23

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccattttgtc tacgggacga                                                 20
```